(12) United States Patent
Oba

(10) Patent No.: US 7,879,869 B2
(45) Date of Patent: Feb. 1, 2011

(54) DRUGS FOR AMELIORATING POSTCIBAL HYPERGLYCEMIA

(75) Inventor: Kenzo Oba, Tokyo (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 1166 days.

(21) Appl. No.: 10/485,217

(22) PCT Filed: Jul. 29, 2002

(86) PCT No.: PCT/JP02/07655

§ 371 (c)(1),
(2), (4) Date: Mar. 4, 2004

(87) PCT Pub. No.: WO03/011308

PCT Pub. Date: Feb. 13, 2003

(65) Prior Publication Data

US 2004/0191209 A1    Sep. 30, 2004

(30) Foreign Application Priority Data

Jul. 30, 2001   (JP) .............................. 2001-229087

(51) Int. Cl.
   *A61K 38/00*    (2006.01)
   *C12Q 1/02*     (2006.01)
(52) U.S. Cl. ........................................ 514/279; 435/29
(58) Field of Classification Search .................... 424/78
   See application file for complete search history.

(56) References Cited

U.S. PATENT DOCUMENTS

| | | | |
|---|---|---|---|
| 5,447,726 A * | 9/1995 | Nomura | 424/464 |
| 5,468,727 A | 11/1995 | Phillips | 514/12 |
| 5,496,545 A | 3/1996 | Holmes-farley | 424/78.11 |
| 5,607,669 A | 3/1997 | Mandeville | 424/78.12 |
| 5,847,008 A * | 12/1998 | Doebber et al. | 514/708 |
| 5,859,051 A * | 1/1999 | Adams et al. | 514/469 |
| 5,980,881 A | 11/1999 | Mitsuka | 424/78.1 |
| 6,562,329 B2 * | 5/2003 | Hadvary et al. | 424/78.08 |
| 2004/0047834 A1 * | 3/2004 | Suzuki et al. | 424/78.1 |

FOREIGN PATENT DOCUMENTS

| | | |
|---|---|---|
| EP | 482498 | 10/1991 |
| JP | 60-209523 | 10/1985 |
| JP | 04-282324 | 10/1992 |
| KR | 1998-702533 | 7/1998 |
| WO | 00/03742 | 1/2000 |
| WO | 00/27401 | 5/2000 |
| WO | 01/25291 | 4/2001 |

OTHER PUBLICATIONS

Garg et al. (Cholestyramine therapy for dyslipidemia in non-insulin dependent diabetes mellitus: a short-term, double-blind, cross-over trial, Annals of Internal Medicine (Sep. 15, 1994, vol. 121, pp. 416-422).*
MCI-196, "Early Phase II Study of MCI-196 in Patients with Hypercholesterolemia", pp. 97-124, pp. 97 and 119 translated, 1996.
The MCI-196 study group, "Clinical Study of MCI-196 for Hypercholesterolemia -A Dose Finding Double-blind Comparative Study", pp. 63-104, pp. 63 and 91 translated, 1996.
An excerpt of the document "Outline of Product Information of CHOLEBINE" with partial translation, 1999.
Notice Requesting Submission of Opinion issued Jul. 29, 2008 in corresponding Korean Patent Application No. 10-2004-7001122, with English translation.
Notice Requesting Submission of Opinion, dated Jun. 29, 2009 in counterpart Korean Application No. 10-2004-7001122, with English translation.
Notice Requesting Submission of Opinion issued Jul. 29, 2008 in corresponding Korean Patent Application No. 10-2004-7001122, with English translation.

* cited by examiner

*Primary Examiner*—Sreeni Padmanabhan
*Assistant Examiner*—Timothy E Betton
(74) *Attorney, Agent, or Firm*—Wenderoth, Lind & Ponack, L.L.P.

(57) ABSTRACT

It is mentioned to provide drugs for ameliorating postcibal hyperglycemia, drugs for inhibiting an increase in blood glucose level and pharmaceutical compositions for preventing or treating diabetes, each containing a pharmaceutically acceptable anion exchange resin typified by colestimide. Thus, it becomes possible to provide drugs clearly exhibiting an effect of inhibiting an increase in postcibal blood glucose level.

2 Claims, 2 Drawing Sheets

DRUGS FOR AMELIORATING POSTCIBAL HYPERGLYCEMIA

This application is a U.S. national stage of International Application No. PCT/JP02/07655 filed Jul. 29, 2002.

TECHNICAL FIELD

This invention relates to drugs for ameliorating postcibal hyperglycemia containing a pharmaceutically acceptable anion exchange resin.

BACKGROUND ART

With regard to an anion exchange resin known as a cholesterol-lowering agent typified by colestimide (trade name: cholebine by Mitsubishi Pharma Corporation)or colestyramine resin (Bristol-Myers Squibb Co.), there was a report on the lowering activity of the blood glucose level after the administration for a certain period of time so far. However, the clear effect has not been observed and the mode of action has not been elucidated. While acarbose (trade name: glucobay by Bayer Yakuhin, Ltd.) and voglibose (trade name: basen by Takada Chemical industries, Ltd.) were at present know as drugs for ameliorating postcibal hyperglycemia, these drugs have no insulin secreting effect. Further, these drugs exhibit relatively frequent adverse effect such as flatulence and increase of flatus. Moreover, compared to the non-absorbable anion exchange resin typified by cholebine, the above-mentioned glucobay has four contraindications and cautions are needed to subject patients.

On the contrary, a pharmaceutically acceptable anion exchange resin which exhibits a clear inhibitory effect on the increase of postcibal blood glucose level in the study on the influence against the diurnal variation of blood glucose level in hypercholesterolemia patients complicated by type II diabetes has not been reported so far as much as the present inventor knows.

DISCLOSURE OF THE INVENTION

The purpose of the present invention is to drugs for ameliorating postcibal hyperglycemia containing a pharmaceutically acceptable anion exchange resin.

As a result that the present inventor has made intensive investigations to achieve the above problem, the present inventor has found that colestimide (2-methylimidazole-epichlorohydrin copolymer) known as a cholesterol-lowering agent exhibited a clear effect of inhibiting an increase in postcibal blood glucose level in the study on the influence against the diurnal variation of blood glucose level in hypercholesterolemia patients complicated by type II diabetes and has completed the present invention.

Namely, the first gist of the present invention lies in a drug for amelioration postcibal hyperglycemia containing a pharmaceutically acceptable anion exchange resin, and a drug for inhibiting an increase in blood glucose level containing a pharmaceutically acceptable anion exchange resin.

As the second gist of the present invention, there includes a pharmaceutical composition for preventing or treating diabetes each containing a pharmaceutically acceptable anion exchange resin as an active ingredient. The preferable example includes that the postcibal hyperglycemia is ameliorate; the increase in postcibal blood glucose level is inhibited; diabetes is type II diabetes; and the diabetes is diabetes as a disease complication in patients with hyperchlolestemia.

In any gist as mentioned above, the pharmaceutically acceptable resin is selected from colestimide, colestyramine resin, colestipol, sevelamer hydrochloride and colesevelam hydrochloride, and the preferable example of the pharmaceutically acceptable resin includes an anion exchange resin synthesized by a polymerization reaction of epichlorohydrin derivative with an amine. More preferable embodiments include the invention wherein the pharmaceutically acceptable anion exchange resin is colestimide.

In any gist as mentioned above, the preferable embodiment includes that the sulfonylurea drugs are used simultaneously, separately or sequentially.

The third gist of the present invention includes a method for ameliorating postcibal hyperglycemia using a pharmaceutically acceptable anion exchange resin, and a method for inhibiting the increase of postcibal blood glucose using a pharmaceutically acceptable anion exchange resin.

BRIEF DESCRIPTION OF THE INVENTION

BEST MODE FOR CARRYING OUT THE INVENTION

Figure 1:
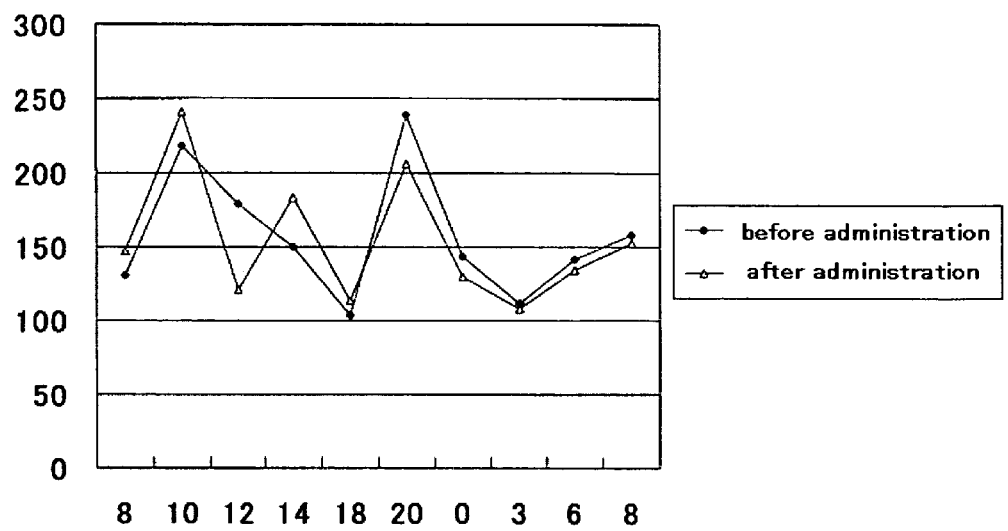
FIG. 1 shows the diurnal variation of the blood glucose level of case 1 in Example 1.

The present invention will be explained in more detail.

According to the present invention, a pharmaceutically acceptable anion exchange resin is an anion exchange resin which can be administered as a drug. The substance is not particularly limited, so far that the substance exhibits the inhibitory effect against the increase of the postcibal blood glucose level in the study of the diurnal variation of the blood glucose level of the patients administered said anion exchange resin as shown in the following examples. One of the example includes colestimide (2-methylimidazole-epichlorohydrin copolymer) as the most preferable example. Colestimide has an irregularly assembled and complicated stereostructure, and is represented by the fundamental structure of the following formula (I) that is partially represented by the following formula (II), and is obtained by the polymerization reaction of an epichlorohydrin derivative with an amine typified by an imidazole derivative, namely by the production method described in Japanese Patent Unexamined Publication (Kokai) No. 60-209523.

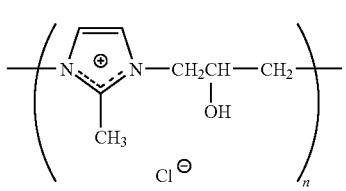

(I)

-continued

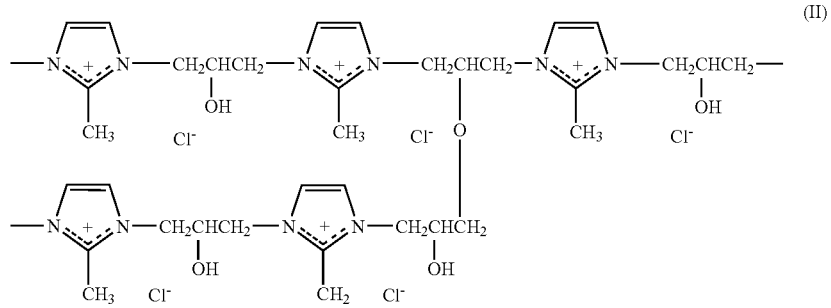

(II)

Examples of other preferable anion exchange resins include chlolestyramine resin as mentioned above and colestipol ((chloromethyl)oxirane-added N-(2-aminoethyl)-N'-[2-[(2-aminoethyl)amino]ethyl]-1,2-ethylenediamine polymer), which are sold by Sigma Inc. The cholestyramine resin is a strongly basic anion exchange resin containing a quaternary ammonium groups added styrene-divinylbenzene copolymer, and its fundamental structure is represented by the following formula (III).

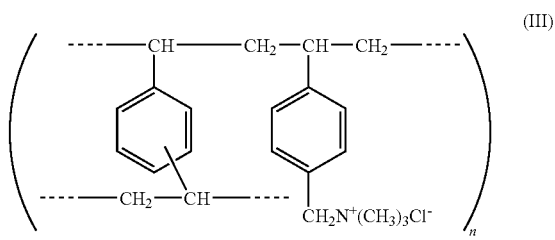

(III)

The fundamental structure of sevelamer hydrochloride is represented by the following formula, and can be prepared by the method described in U.S. Pat. No. 5,496,545 or a similar method thereto.

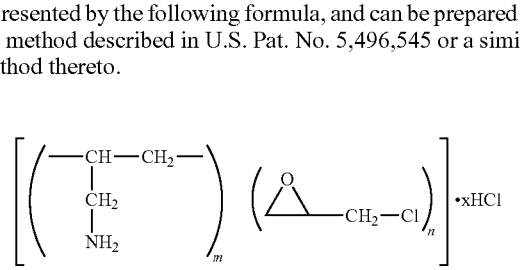

The fundamental structure of colesevelam hydrochloride is represented by the following formula, and can be prepared by the method described in U.S. Pat. No. 5,607,669 or a similar method thereto.

In addition, anion exchange resins described in Japanese Patent Publication of International Application (Kohyo) Nos. 9-504782, 9-500368, 10-501264, 10-501842, 11-507093, 11-512074, and 5-512332, and Japanese Patent Unexamined Publication (Kokai) Nos. 8-208750, 9-202732, 10-114661, and 11-228449 can be used in the present invention, as long as they are not beyond the gist of the present invention.

The above compound itself, an active ingredient, can be used as drugs for ameliorating postcibal hyperglycemia. It is preferably that a pharmaceutical composition containing the above active ingredient is manufactured by using an additive for a pharmaceutical preparation used widely, and then uses the same.

Such pharmaceutical compositions include tablets, capsules, fine granules, pills, troches and liquids, and the are orally administered (a sublingual administration may be included).

The pharmaceutical composition for oral administration can be manufactured by a conventional method used widely, such as mixing, filling or compressing. Further, by applying repeated formulation procedures, the active ingredient may be distributed in a pharmaceutical composition containing a large amount of the excipient. For example, tablets or capsules used for the oral administration are preferably provided as unit dosage forms, and they may contain carriers for the pharmaceutical preparations used conventionally, such as binder, a filling material, a diluent, a compressing agent, a lubricant, a disintegrator, a coloring agent, a flavoring agent, and a moistening agent. A tablet may be manufactured, for example, as a coated tablet according to a well-know method in the art by using a coating agent.

Examples of the preferably filling material include cellulose, mannitol, lactose or the like. Starch, polyvinylpyrrolidone, a starch derivative such as sodium starch glycolate or the like as a disintegrator, and sodium lauryl sulfate or the like as a lubricant can be used as additives for the pharmaceutical preparation. A pharmaceutical composition in the form of a liquid for oral administration is provided as, for example, a pharmaceutical composition such as an aqueous or oily suspension, a solution, an emulsion, a syrup or an elixir; or a dry

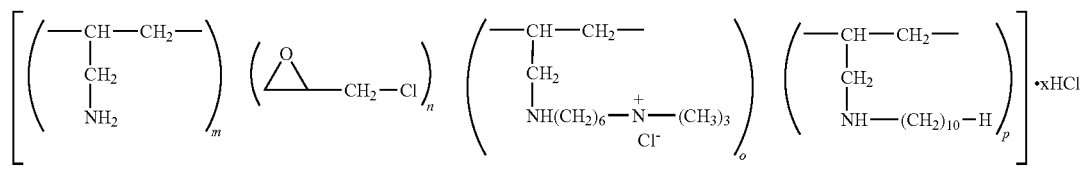

pharmaceutical composition which can be re-dissolved in water or an appropriate medium before use.

In the liquids, additives commonly used may be added such as, for example, a precipitating preventing agent such as sorbitol, syrup, methyl cellulose, gelatin, hydroxyethylcellulose, carboxymethylcellulose, aluminum stearate gel or hydrogenated edible fat; an emulsifier such as lecithin, sorbitan monooleate or acacia; an oily ester such as almond oil, refined coconut oil or a glycerin ester; a non-aqueous medium such as propylene glycol or ethyl alcohol (edible oil may be included); a preservative such as methyl ester, ethyl ester or propyl ester or p-hydroxybenzoic acid, or sorbic acid; and, if necessary, a conventionally flavoring agent or coloring agent.

The above pharmaceutical composition or oral administration such as in the form of tablets, capsules, fine granules or the like generally contain 5 to 95% by weight, preferably 25 to 90% by weight of the active ingredient.

Colestimide has been sold by Mitsubishi Pharma Corporation as a trade name of "cholebine", and cholebine, per se, can be used for the present invention.

Dose of the drugs for ameliorating postcibal hyperglycemia of the present invention may appropriately determined depending upon the active ingredient use, the age, health conditions, body weight of the patient, severity of the disease, a type and frequency of the simultaneous therapy or treatment, a nature of the desired effects and the like. In general, daily dose for the adult may range 1 to 60 g as a weight of the active ingredient, and the drugs may be administered once or several times a day.

In the present invention, the above pharmaceutically acceptable anion exchange resin and a sulfonylurea drug may be used simultaneously, separately or sequentially. Described specifically, a drug containing the above anion exchange resin as an effective ingredient and a sulfonylurea drug maybe be administered as one pharmaceutical composition or as respective pharmaceutical compositions, based on the dose adjusted, depending on the age, condition, sex, symptoms, or the like of a patient as needed. In the latter case, they may be administered simultaneously in the same dosage form or different dosage forms; administered sequentially on the same day in the same dosage form or different dosage forms; or administered at regular intervals for several days, several weeks or several months, depending on the age, condition, sex, symptoms or the like of a patient.

The sulfonylurea drugs are not specifically limited and, in more detail, include the drugs exhibiting the inhibitory effect against the increase of blood glucose level as shown in the example hereinafter, and, for example, tolbutamide (trade name: diabetose/Nippon Iyakuhin Kogyo K.K., Diaben/Chugai Pharmaceutical Co., Ltd.), glimepiride (trade name: amaryl/Aventis Pharma), gliclazide (trade name: glimicron/Dianippon Pharmaceutical Co., Ltd.), and glibenclamide (trade name: euglucon/Nippon Roche, Yamanouchi Pharmaceutical Co. Ltd.) are exemplified. As these sulfonylurea drugs, the already marketed reagents or drugs can be used.

EXAMPLE

The present invention will be explained according to the following examples in more detail. It should however be borne in mind that the present invention is not limited by them. Colestimide used in the following examples is 70% cholebine granule which is sold by Mitsubishi Pharma Corporation.

Example 1

(Subject and Method)

Influences of colestimide administration on the diurnal variations of serum lipid level and blood glucose level were investigated before and after administration in the same case by using, as subjects, inpatients (adults, either female or male) who had suffered from hypercholesterolemia complicated by type 2 diabetes, and whose calorie intake had been controlled strictly and blood lipid level and blood glucose level had been grasped.

The diurnal variations of blood glucose level were measured at ten time points in total. They were "before breakfast (at 8:00), two hours after breakfast (at 10:00), before lunch (at 12:00), two hours after lunch (at 14:00), before dinner (at 18:00), two hours after dinner (at 20:00), at 0:00, at 3:00, at 6:00 and at 8:00 in the next morning".

The test was performed in accordance with the following schedule:
(1) Period of observation: 2 weeks after hospital stay is started
    In the period of observation, it was confirmed that the patients had maintained stable serum lipid level, serum glucose level, body weight and the like.
(2) Period of treatment: two weeks after the administration of colestimide was started.
    The diurnal variation of serum lipid level and blood glucose level of the patients under administration with colestimide for 2 weeks were compared with those of the patients in the period of observation.

(Test Drug, Administration Manner and Amount)

Colestimide was administered before breakfast and before lunch, that is, twice a day, each 1.5 g.

(Diet Therapy and Drugs Used in Combination)

Throughout the periods of observation and treatment, the caloric intake was fixed (25 to 30 kcal per kg of a standard weight). When anti-hyperlipidemia drugs other than colestimide (such as an HMG-CoA reductase inhibitor, a fibrate drug, probucol (generic name, "Lorelco", trade name; product of Otsuka Pharmaceutical Co., Ltd.), and "Sinlestal" (product of Daichi Pharmaceutical Co.; Ltd.)) had still been administered, their administration was continued without changing the administration manner and amount throughout the periods of observation and treatment and additional administration the periods of observation and treatment and an influence on the serum lipid level were administered without changing the administration manner and amount throughout the periods of observation and treatment, while drugs which might have an influence on the blood glucose level (such as an α-glucosidase inhibitor and an insulin resistance improver) were not administered in principle. when a sulfonylurea drug had already been administered, however, its administration was continued without changing the administration manner and amount throughout the periods of observation and treatment. Also, the other drugs possible throughout the periods of observation and treatment.

(Results)

Details of the subjects and results of the therapy will next be described. In the following data, TC means the total cholesterol level, HDL-C means the HDL-cholesterol level, and TG means the triglyceride level. The numbers before and after the arrow are their levels before and after colestimide administration, each in unit of mg/dL. In all the graphs, ? shows the blood glucose level before colestimide administration and ? shows the blood glucose level after colestimide administration. Time points (blood collection time) are plotted on the abscissa, while the blood glucose level (mg/dL) is plotted on the ordinate.

Case 1: 75-year old male administered with tolbutamide (generic name; 500 mg/day)
TC: 210 ? 152, TG: 74 ? 75
The diurnal variations of his blood glucose level are shown in FIG. 1.

Figure 2:
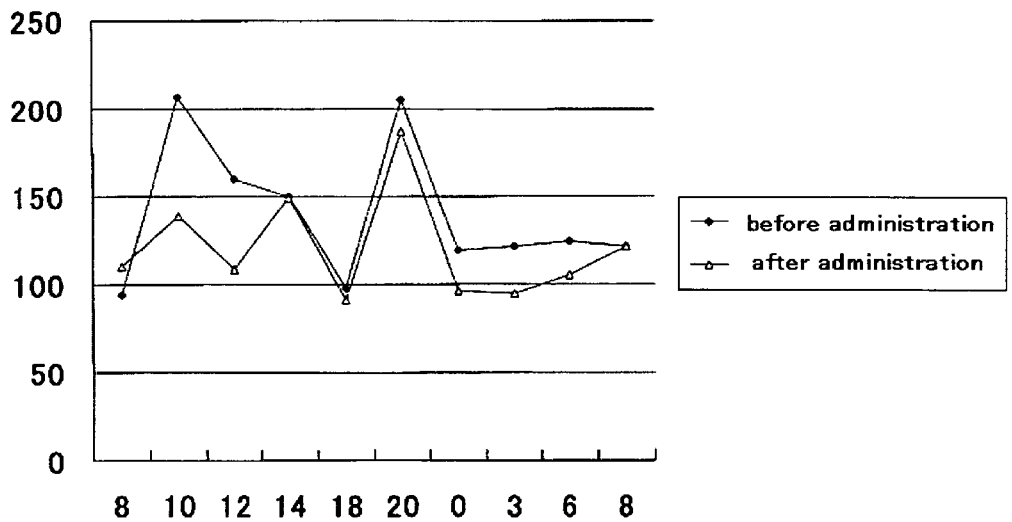
FIG. 2 shows the diurnal variation of the blood glucose level of case 2 in Example 1.

Case 2: 63-year old male subjected to only diet therapy
TC: 204 ? 142, HDL-C: 38 ? 33, TG: 221 ? 146
The diurnal variations of his blood glucose level are shown in FIG. 2.

Figure 3:
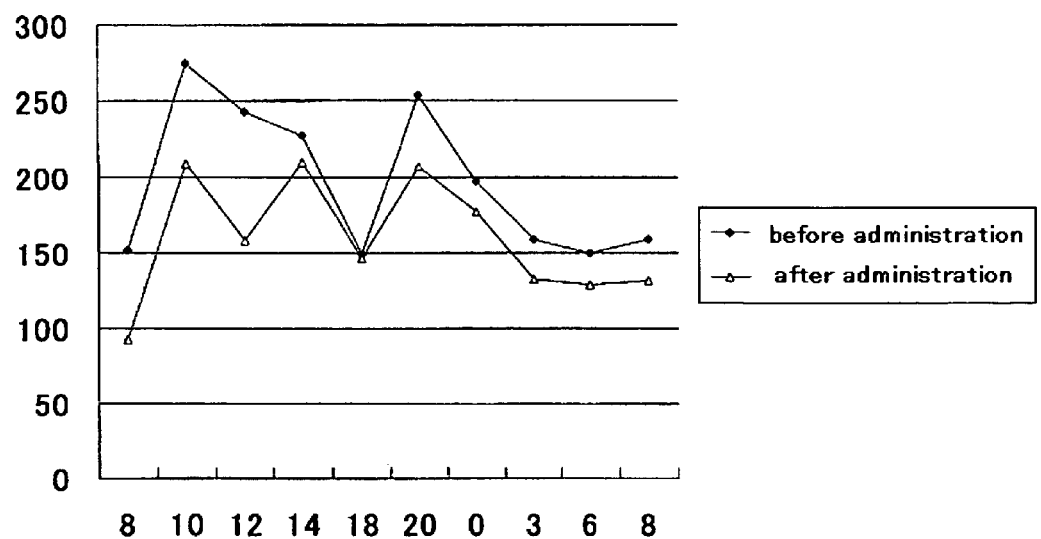
FIG. 3 shows the diurnal variation of the blood glucose level of case 3 in Example 1.

Case 3: 78-year old male subjected to only diet therapy
TC: 188 ? 155, HDL-C: 44 ? 40, TC: 176 ? 168
The diurnal variations of his blood glucose level are shown in FIG. 3.

Figure 4:
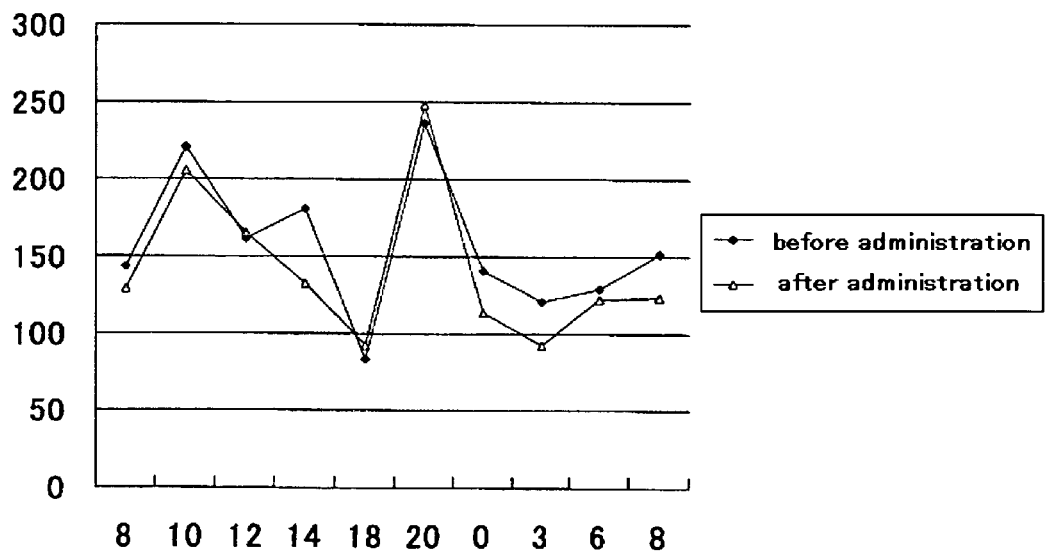
FIG. 4 shows the diurnal variation of the blood glucose level of case 4 in Example 1.

Case 4: 73-year old male administered with glimepiride (generic name; 1 mg/day)
TC: 242 ? 198, HDL-C: 66 ? 66, TG: 100 ? 84
The diurnal variations of his blood glucose level are shown in FIG. 4.

It is apparent from the results of Case 2 and Case 3 that single administration of colestimide is effective for inhibiting a postcibal increase in the blood glucose level, and from the results of Case 1 and Case 4 that use of colestimide and a sulfonylurea drug in combination is also effective for inhibiting a postcibal increase in the blood glucose level.

INDUSTRIAL APPLICABILITY

According to the present invention, drugs which clearly exhibit the inhibitory effect on the postcibal blood glucose level are obtained. Further, the drugs of the present invention with the combination of the sulfonylurea drugs show the inhibitory effect on the postcibal blood glucose level.

The present application was filed with claiming the conventional priority based on Japanese Patent Application No. 2001-229097. All of the patent bulletins, patent publication (Kokai) bulletins, literatures cited in eth specification can be used alone or in combination thereof as the references of the present invention.

The invention claimed is:

1. A method for ameliorating postcibal hyperglycemia consisting of administering a therapeutically effective amount of colestimide as the active ingredient to a patient in need thereof.

2. A method for inhibiting an increase in postcibal blood glucose level, consisting of administering a therapeutically effective amount of colestimide as the active ingredient to a patient in need thereof.

* * * * *